(12) United States Patent
Nielsen

(10) Patent No.: US 8,406,884 B2
(45) Date of Patent: Mar. 26, 2013

(54) EXTERNAL DEVICE THAT CONTINUOUSLY MONITORS FOR OSDB AND DELIVERS AUDIO STIMULATION THERAPY

(75) Inventor: Larry Nielsen, Burlington, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 484 days.

(21) Appl. No.: 12/279,998

(22) PCT Filed: Feb. 6, 2007

(86) PCT No.: PCT/US2007/061638
§ 371 (c)(1), (2), (4) Date: Aug. 20, 2008

(87) PCT Pub. No.: WO2007/100958
PCT Pub. Date: Sep. 7, 2007

(65) Prior Publication Data
US 2010/0228315 A1    Sep. 9, 2010

Related U.S. Application Data

(60) Provisional application No. 60/777,480, filed on Feb. 28, 2006.

(51) Int. Cl.
*A61N 1/36* (2006.01)
(52) U.S. Cl. .......................................... 607/42; 607/136
(58) Field of Classification Search .................. 607/1–3, 607/42, 26–28, 55; 128/633
See application file for complete search history.

(56) References Cited

U.S. PATENT DOCUMENTS

| | | | |
|---|---|---|---|
| 4,644,330 A | 2/1987 | Dowling | |
| 5,673,692 A * | 10/1997 | Schulze et al. | 600/301 |
| 5,853,005 A | 12/1998 | Scanlon | |
| 6,062,216 A | 5/2000 | Corn | |
| 6,253,871 B1 | 7/2001 | Aceti | |
| 6,283,915 B1 | 9/2001 | Aceti et al. | |
| 6,363,270 B1 | 3/2002 | Colla et al. | |
| 6,454,718 B1 * | 9/2002 | Clift | 600/483 |
| 6,473,511 B1 | 10/2002 | Aceti et al. | |
| 6,473,651 B1 * | 10/2002 | Kuzma et al. | 607/57 |
| 6,544,199 B1 | 4/2003 | Morris | |
| 6,808,473 B2 * | 10/2004 | Hisano et al. | 482/8 |
| 7,748,493 B2 * | 7/2010 | Moses et al. | 181/129 |
| 2002/0072781 A1 * | 6/2002 | Lattner et al. | 607/42 |
| 2003/0139658 A1 * | 7/2003 | Collier et al. | 600/407 |
| 2003/0195588 A1 * | 10/2003 | Fischell et al. | 607/55 |
| 2003/0199945 A1 * | 10/2003 | Ciulla | 607/48 |
| 2004/0081328 A1 | 4/2004 | Leedom et al. | |
| 2004/0134496 A1 * | 7/2004 | Cho et al. | 128/204.23 |
| 2004/0240695 A1 | 12/2004 | Leedom et al. | |
| 2005/0059870 A1 * | 3/2005 | Aceti | 600/340 |

(Continued)

FOREIGN PATENT DOCUMENTS

| | | |
|---|---|---|
| DE | 19904260 A1 | 11/2000 |
| WO | 2005020841 A2 | 3/2005 |

*Primary Examiner* — Carl H Layno
*Assistant Examiner* — Paula J Stice

(57) ABSTRACT

A physiological parameter measuring device (14) is disposed within or near an ear canal of a subject (16) to non-invasively sense at least one physiological parameter of the subject which one physiological parameter is associated with at least one physiological condition of the subject. An analyzing device (48) is operatively coupled to the physiological parameter measuring device (14) to analyze the sensed physiological parameter and detect the physiological condition of the subject (16). Based on the detection and analysis of the physiological condition of the subject (16), a stimulating device (20) stimulates the subject (16) with the physiological parameter measuring device (14) within or near the ear canal of the subject (16) to mitigate the physiological condition of the subject (16).

23 Claims, 3 Drawing Sheets

U.S. PATENT DOCUMENTS

| | | |
|---|---|---|
| 2005/0061319 A1 | 3/2005 | Hartley et al. |
| 2005/0119711 A1* | 6/2005 | Cho et al. ......................... 607/42 |
| 2005/0177051 A1* | 8/2005 | Almen .......................... 600/509 |
| 2006/0047201 A1* | 3/2006 | Eide .............................. 600/485 |

* cited by examiner

EXTERNAL DEVICE THAT CONTINUOUSLY MONITORS FOR OSDB AND DELIVERS AUDIO STIMULATION THERAPY

BACKGROUND OF THE INVENTION

The following relates to monitoring arts. It finds particular application in conjunction with monitoring and treating of Obstructive Sleep Disordered Breathing (OSDB). It finds more particular application in monitoring and treating sleep apnea and will be described with a particular reference thereto. However, it is to be appreciated that the following is also applicable to monitoring and treatment of other physiological conditions.

Snoring typically manifests OSDB. OSDB includes upper airway resistance syndrome, non-obstructive and obstructive sleep apneas and nocturnal Cheyne-Stokes breathing. While snoring is characterized by partial occlusion of the upper airway passage during sleep, the sleep apnea and Cheyne-Stokes breathing is normally characterized by intermittently complete occlusions.

Sleep apnea is the most common piece of OSDB and is characterized by the absence of breathing for a certain period of time such as 30 to 45 seconds. Doctors estimate that about 18 million Americans suffer from sleep apnea. One cause for sleep apnea is an obstruction of the airway when the muscles of the tongue or uvula relax. Obesity and an abnormal amount of fat in the throat area are conducive to this condition. Another cause is a temporary cessation of the message from the brain that tells the diaphragm to breathe. In sleep apnea, with each period of breathlessness, which can be as many as twenty in an hour, the carbon dioxide level in the blood rises. There is a corresponding decrease in the blood oxygen levels. This, along with the stress and the struggle to draw breath, puts a strain on the heart. Untreated, sleep apnea can cause high blood pressure and other cardiovascular disease, memory problems, weight gain, impotency, and headaches. If the sleep apnea is diagnosed and treated sooner, such problems might be avoided in some cases, or at least the damage might be reduced.

Polysomnography is a standard diagnostic approach to detect the sleep apnea. It requires the person to stay overnight in the hospital for observation. A polysomnographic procedure involves tethered connections and monitoring of many parameters which makes it intensive, site dependent, and costly. Such approach is not practical for screening a large number of patients and thus the majority of patients suffering from OSDB remain undiagnosed.

One approach to treat sleep apnea is to use a face mask and a small air compressor or fan that forces just enough air through the nasal passages to keep the nasal passages open during the night. But, although such a mask allows a good night's sleep, it causes physical discomfort to the person as well as makes the person prone to nasal congestion and infections.

Another approach is to pace the heart at a faster rate, which stimulates the sleeper's breathing. Unfortunately, this requires an implantable pacemaker type device to the heart.

Another approach is to pace or stimulate the muscles of the tongue or uvula from relaxation thus opening the constricted airway allowing the sleeper to resume breathing. Unfortunately, this approach requires an implantable nerve or muscle stimulator.

Another approach is to surgically remove a portion of the posterior tongue or uvula muscles so that when the muscles relax the airway remains sufficiently open to not totally occlude airflow. Unfortunately, this approach requires a surgical procedure and has not been proven to be a long-term solution.

In yet another approach, the nerves are stimulated by a high voltage shock to the sleeper to condition the sleeper to resume breathing. Such method is painful and might result in a nervous injury.

BRIEF SUMMARY OF THE INVENTION

The present application provides new and improved imaging apparatuses and methods, which overcome the above-referenced problems and others.

With reference to one aspect, a monitoring, therapy, and polysomnography testing system is disclosed. A physiological parameter measuring device is disposed within or near an ear canal of a subject to non-invasively sense at least one physiological parameter of the subject which one physiological parameter is associated with at least one physiological condition of the subject. An analyzing device is operatively coupled to the physiological parameter measuring device to analyze the sensed physiological parameter and detect the physiological condition of the subject. Based on the detection and analysis of the physiological condition of the subject, a stimulating device stimulates the subject with the physiological parameter measuring device within or near the ear canal of the subject to mitigate the physiological condition of the subject.

With reference to another aspect, a method is disclosed. At least one physiological parameter of a sleeping subject is non-invasively sensed via an auditory canal of the subject, the physiological parameter being associated with at least one physiological condition of the subject.

The sensed physiological parameter is analyzed to detect the physiological condition of the subject. In response to the detection of the physiological condition of the subject, the subject is stimulated so that the physiological condition of the subject is mitigated.

With reference to another aspect, a system for monitoring and treating obstructive sleep disordered breathing (OSDB) is disclosed. An in-the-ear sensing device is disposed within an ear canal of a subject to non-invasively sense at least one physiological parameter of the subject which one physiological parameter is associated with the OSDB. A monitoring device is operatively coupled to the in-the-ear sensing device to communicate with the in-the-ear sensing device. An analyzing device analyzes the sensed physiological parameter and detects an OSDB event. A device is disposed in the in-the-ear sensing device, which device, based on the detected OSDB event, stimulates the subject to mitigate the OSDB event.

Still further advantages and benefits of the present application will become apparent to those of ordinary skill in the art upon reading and understanding the following detailed description of the preferred embodiments.

The following may take form in various components and arrangements of components, and in various steps and arrangements of steps. The drawings are only for purposes of illustrating the preferred embodiments and are not to be construed as limiting.

BRIEF DESCRIPTIVE VIEWS OF THE DRAWINGS

DETAILED DESCRIPTION OF THE INVENTION

Figure 1:
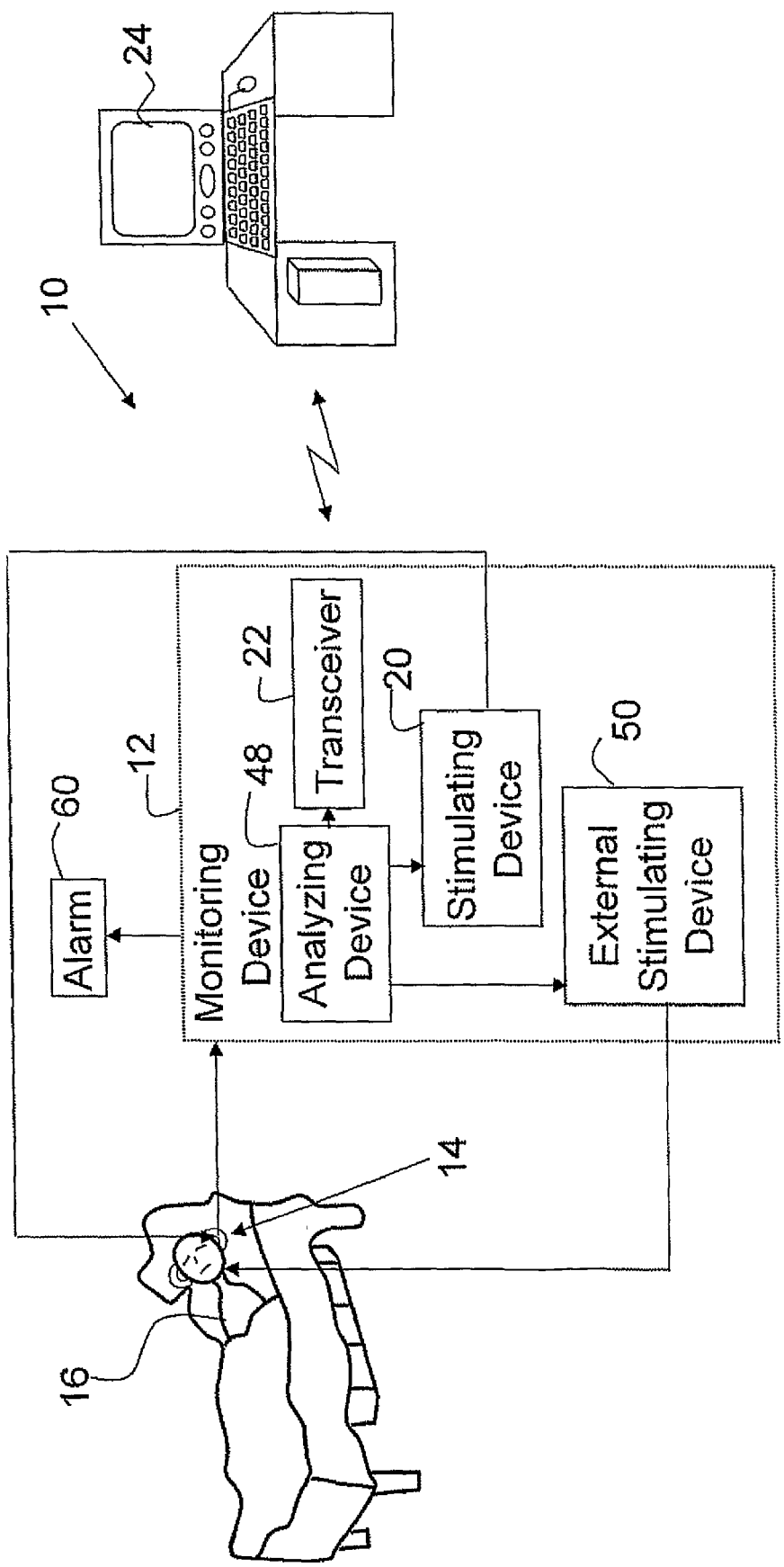
FIG. 1 is a diagrammatical illustration of a monitoring and therapy system.
Figure 2:
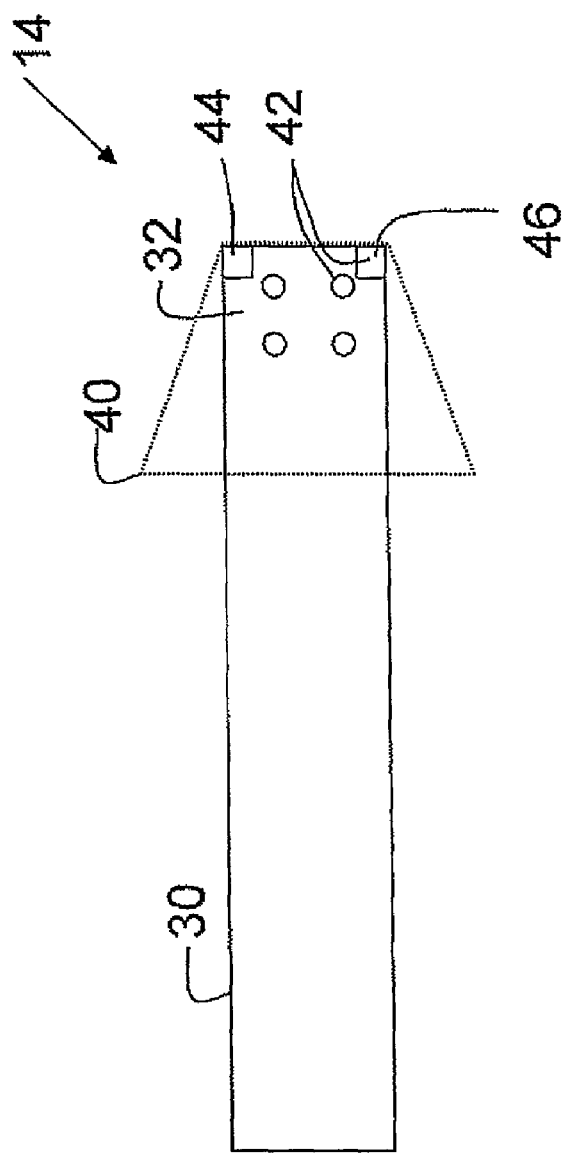
FIG. 2 is a diagrammatical illustration of an in-the-ear probe.
Figure 3:
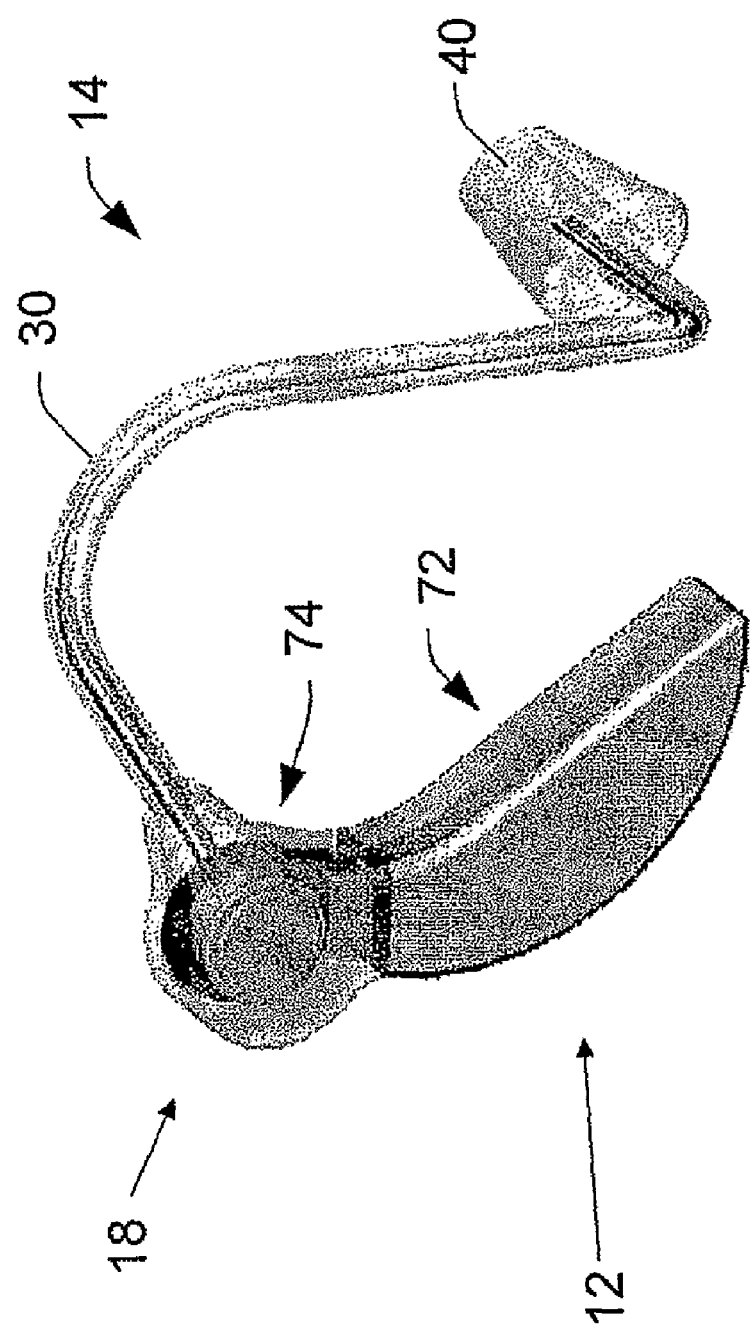
FIG. 3 is an image of an in-the-ear probe attached to a behind-the-ear device.

With reference to FIGS. 1, 2 and 3, a monitoring or therapy or Polysomnography testing system 10 includes a monitoring device 12 that is configured to communicate with physiological measuring devices, such as an in-the-ear probe (ITE) 14, inserted in an ear or auditory canal of a subject or sleeper 16, for measuring one or more physiological parameters or signals, such as respiration, blood pressure, pulse oximetry or a level of blood oxygen (SpO$_2$), heart or pulse rate, perfusion, and temperature, from within an ear or auditory canal. As described in detail below, the monitoring device 12 monitors one or more physiological signals provided by the probe 14 to detect signs of Obstructive Sleep Disordered Breathing (OSDB) such as the signs of sleep apnea. If the signs of sleep apnea are detected, a stimulating device 20 applies stimulus to the subject 16 via the probe 14 so that a normal breathing pattern is restored. The examples of the monitoring device 12 are a behind-the-ear (BTE) OSDB monitoring device 18 as shown in FIG. 3, an on-a-collar (OAC) device, and any other device suitable for interpreting the measurements and providing a suitable therapy as described below.

For example, the physiological parameters may be wirelessly transmitted by a wireless transceiver 22, for example, continuously, periodically at a predetermined rate, on-demand, and upon occurrence of an event, from the monitoring device 12 to a computerized unit or central station 24. The computerized unit 24 may be used to record the entire sleep activity and/or only the number and severity of OSDB events. Diagnostic analysis may be performed as data is received, or the recorded activity may be logged within a clinical or home environment and then physically or electronically returned to the Polysomnography Lab the next day for diagnostic analysis. The number of stimulation corrected OSDB events, non-corrected OSDB events, along with event severities may additionally be recorded.

With continuing reference to FIG. 2, the probe 14 includes a tube 30 that inserts into the ear canal of the subject 16. The tube 30 is suitably dimensioned to enter the ear canal to a suitable depth and adapts to various shaped ear canals, e.g., different diameter or contours.

In one embodiment, the tube 30 includes an end portion 32, which resides in the ear canal. An inflatable balloon 40 surrounds the end portion 32 of the tube 30 or any other suitable portion of the tube 30. The inflatable balloon 40 supports one or more sensors 42 that are operatively coupled to a surface of the balloon 40 to measure physiological signals. The examples of sensors include light emitting diodes (LEDs), an infrared (IR) source, light detecting sensors, a pressure transducer, a microphone, a speaker, and a thermistor. For example, the light detecting sensor is used to minimize or prevent absorption of light not indicative of the physiological process under measurement such as light from outside the ear or light emitted from another sensor located on the balloon 40. The inflatable balloon 40 is inflated to position the sensors 42 proximate to an appropriate tissue within the ear canal with adequate force and pressure to ensure close coupling of sensors with the tissue but without causing decreased perfusion or blanching of the tissue. Alternatively, the balloon is omitted and replaced with a spongy material that expands to correctly position the sensors. The sensors 42 are mounted about the end portion 32 of the tube 30 and could be moved into contact with the tissue once the tube 30 is inserted into the ear canal of the subject 16.

Typically, sensors for measuring pulse rate and/or blood oxygen are positioned proximate to the ear canal tissue that is perfused with arterial blood supplied by branches of the External as well as the Internal Carotid Arteries, thus serving as a well perfused physiological site even if the body is experiencing peripheral shutdown due to shock or other conditions. Such sensors include an energy emitting means, such as an LED, which emits light into the tissue, and an energy detecting means that detects light transmission through the vascular tissue to determine pulse rate and/or blood oxygen levels. In another example, a temperature sensor, such as a thermistor, is positioned proximate to the vascular tissue. In yet another example, sensors for sensing audio signals such as a microphone 44 are suitably positioned in relatively quite regions of the ear canal to mitigate sensing erroneous audio signals. For example, microphone 44 can sense pulse pressure sounds and respiration. As another example, sensor(s) for producing audio signals, such as a speaker 46, are positioned in the ear canal to produce audio signals to restore the sleeper's breathing pattern as described below.

The inflatable balloon 40 is also used to facilitate non-invasive measuring of the blood pressure. For the non-invasive blood pressure measurement, the inflatable balloon 40 is inflated until it occludes blood flow in a portion of the ear proximate a blood pressure sensor(s), such as a pressure transducer, operatively connected to the inflatable balloon 40. The pressure in the inflatable balloon 40 is then suitably released to deflate the inflatable balloon 40. A systolic and a diastolic blood pressure are obtained during inflation and/or deflation using an auscultatory approach via the microphone 42 operatively connected to the balloon 40 and/or an oscillometric approach via optical sensing components attached to the balloon 40.

With reference again to FIG. 1, the probe 14 senses at least a respiration rate of the sleeper 16. In one preferred embodiment, in addition to sensing the respiration of the sleeper 16, the probe 14 senses at least one of a blood oxygen level (SpO$_2$) and the pulse rate of the sleeper 16. In another preferred embodiment, the probe 14 senses at least one of SpO$_2$ and a blood pressure of the sleeper 16. Although blood oxygen level is highly correlated with the severity of the sleep apnea due to the cyclic depression of blood oxygen as the sleeper experiences repeated cycles of oxygen deprivation, analyzing the combination of the respiration rate, blood oxygen level and pulse rate substantially enhances diagnostics of the sleep apnea as compared to analyzing a single signal. An analyzing device 48 analyses the sensed information for sleep apnea, e.g. for absence of breathing. Typically, as the sleeper 16 goes into the sleep apnea, the respiration ceases and SpO$_2$ begins to decrease. The pulse rate typically begins to decrease also. In one embodiment, the analyzing device or algorithm or means 48 analyses combination of data which is received by measuring respiration, SpO$_2$ and the pulse rate, which makes the analysis less susceptible to noise and mistake. The analysis might vary from one sleeper to another depending on that sleeper's personal data and medical history. For example, the pulse rate and SpO$_2$ can be compared with thresholds, e.g. a sudden slowing of the pulse rate by 10 beats per minute and a SpO$_2$ dropping below 90. Based on the analysis, the simulating device 20 applies the stimulus to the sleeper 16. For example, for some subjects the stimulus is given after the respiration cessation of 10 seconds, while for others, the stimulus is given after the respiration cessation of 5 seconds, and in yet for others after a longer duration such as 30 or 45 seconds. As another example, for some sleepers the stimulus is given if the sleeper's pulse rate drops below a predetermined value. As another example, the respiration threshold varies dynamically with $SpO_2$ level or decreases in the pulse rate, e.g. carbon dioxide builds up in the blood shorter respiration cessations are tolerated.

The stimulus is given via the speaker 46, which is, for example, a low power speaker which produces audible sounds that are loud enough to be heard by the user of the device, e.g. the sleeper 16, but are not audible outside of the ear canal of the sleeper 16. For example, the stimulus is a sound or a person's voice that tells the sleeper 16 to start breathing, or to move, e.g. to turn on the side. As about 50% of sleepers with OSDB only show signs of OSDB when sleeping in a supine position, simply telling the sleepers to turn on the side is highly effect for this group. Such stimulus is given subconsciously, by barely waking up the sleeper 16, if at all, only to resume breathing. Such stimulus occurs only a few seconds into the sleep apnea, thus significantly reducing the sleep apnea time. If the apnea persists, a louder voice or noise may be applied. Alternatively, the stimulating device 20 provides an external stimulus to the sleeper 16, e.g. near the sleeper's ear. If the monitoring device 12 determines that after the stimulus is given there has been no breathing for a predetermined period of time, such as 1 minute or more, and the saturation levels are decreasing, the stimulating device 20 progressively increases the intensity of the audio signal. If, after reaching the maximum stimulation signal strength, the monitoring device 12 still does not detect that the breathing has been resumed, in one embodiment, an external stimulating device 50 applies a shock to the neck area or behind the ear via, for example, the on-a-collar device. In another embodiment, an external alarm 60 is provided which awakens, for example, a care provider.

With reference again to FIG. 2, the tube 30 includes one or more passageways (not shown) that extend through the tube 30. Such passageways house sensor data, power, and control wires, provide a hermetically sealed channel for inflating/deflating the balloon 40, and/or allow pressure inside the ear to equalize with the environment during balloon inflation/deflation. The passageways isolate the wires from the inner ear environment, mitigating contamination of both the ear and the sensor wiring and provide a pressurized air conduit to the balloon 40.

With reference again to FIG. 3, the ITE probe 14 is mechanically and electrically coupled to the exemplary behind-the-ear (BTE) device 18, together forming the complete OSDB monitoring device 12. In one instance, the tube 30 and the BTE device 12 are formed as a single unit, while in another instance the tube 30 and the BTE device 12 are detachably connected. Such attachment can be through a fastening means including a threaded connector, a snap, a setscrew, an adhesive, a rivet, etc. An arm 72 provides support behind the ear and a battery 74 powers both devices. An optional sheath (not shown) can be placed over the tube 30 and/or balloon 40 to protect the ear and the structure/balloon/sensor assembly from contamination. In one aspect, the sheath can be semi-permeable to allow airflow, but prevent fluid from moving from one side of the sheath to the other side. In another aspect, the sheath prevents substantially all matter from moving from one side of the sheath to the other side. The structure/balloon/sensor assembly can be disposable, washable, and/or sterilizeable.

In one embodiment, the monitoring device 12 communicates with the central station or computerized unit 24 to receive, display, analyze, validate and forward via wire or wirelessly physiological measurements continuously over a network, spot-check received physiological measurements obtained by the in-the-ear probe and download such measurements to the central monitoring station 24, send information such as, physiological measurements, patient history, medical history, messages, notifications, alarms, and the like to an authorized individual, the central monitoring station, the polysomnography testing center, and the like. Of course, it is contemplated that a plurality of the monitoring devices 12, each associated with a corresponding subject, communicates with the central station or computerized unit 24.

In the manner described above, all necessary physiological signals needed for monitoring OSDB are obtained from one site within the ear. The described embodiments have the ability to treat OSDB from within the ear using audio stimulation therapy. The audio stimulation therapy signal may be programmed to become progressive louder and louder until the sleeper either subconsciously or consciously is momentarily semi-awakened causing the sleeper to breath. The audio stimulation therapy signal can be directed at the sleeper only, allowing others to not be awakened. Monitoring and delivery of therapy for OSDB can be provided that does not consciously arouse the sleeper or cause discomfort or stress that leads to the person's incompliance and non-acceptance. An apnea prone sleeper's discomfort is greatly reduced because the annoying breathing mask is no longer required while sleeping. The detection and treatment of OSDB can be performed without tethered connections (air hose, physiological measurement cables) between the sleeper and external contraptions thus enabling sleeper's movement and position changes during the night. The need for an implanted electrical stimulator or surgical procedures to treat OSDB is eliminated.

The polysomnography diagnostic testing is simplified by eliminating all tethered attachments from external devices to the sleeper and by having all physiological measurements performed from a single site. The cost and complexity of Polysomnography is reduced, making it more practical for screening large numbers of people in Polysomnography Labs. Polysomnography diagnostic testing becomes practical to be performed within the homes of people allowing them to sleep and be tested in their normal sleeping environment. Additionally, it becomes practical to record the number and severity of MB events (corrected and non-corrected) within the home environment to evaluate the need for continuous monitoring for OSDB as well as evaluating the performance of such corrective devices.

The application has been described with reference to the preferred embodiments. Modifications and alterations may occur to others upon reading and understanding the preceding detailed description. It is intended that the application be constructed as including all such modifications and alterations insofar as they come within the scope of the appended claims or the equivalents thereof.

The invention claimed is:

1. A monitoring and therapy system comprising:
an in-the-ear canal probe configured to be disposed within the ear canal of a subject and configured to non-invasively sense at least one physiological parameter of the subject with at least one sensor, wherein the at least one physiological parameter is indicative of respiration cessation of the subject, and wherein the in-the-ear canal probe includes an inflatable balloon configured to position the at least one sensor proximate to tissue within the ear canal upon inflation, the at least one sensor operatively coupled to a surface of the balloon;
an analyzing device operatively coupled to the in-the-ear canal probe, wherein the analyzing device is configured to analyze the at least one sensed physiological parameter and configured to determine respiration cessation of the subject based on the analysis; and a stimulating device configured to stimulate the subject with the in-the-ear canal probe to mitigate the respiration cessation of the subject, wherein the stimulating is based on the determination and includes providing an audible message to the subject without waking the subject, wherein the audible message reminds the subject to breath and/or turn on a side of the subject.

2. The system as set forth in claim 1, wherein the at least one sensed physiological parameter includes respiration by the subject and, when the respiration cessation is determined by the analyzing device, the stimulating device stimulates the subject to resume respiration.

3. The system as set forth in claim 2, wherein the analyzing device is configured to compare the sensed respiration with a physiological threshold and configured to determine the respiration cessation based on the comparison, wherein the stimulating device is configured to stimulate the subject so that the subject resumes respiration.

4. The system as set forth in claim 2, wherein the at least one sensed physiological parameter further includes at least one of blood oxygen level ($SpO_2$), pulse, and blood pressure, wherein the sensors are disposed on an exterior of the in-the-ear canal probe.

5. The system as set forth in claim 4, wherein the analyzing device is configured to compare a combination of at least the sensed respiration, the sensed blood oxygen level ($SpO_2$) and the sensed pulse with a combination of physiological thresholds and configured to determine the respiration cessation based on the combined analysis to minimize a number of erroneous stimulations, and wherein the stimulating device is configured to stimulate the subject so that the subject resumes respiration.

6. The system as set forth in claim 2, further including:
a speaker configured to be disposed in the in-the-ear canal probe, wherein the speaker is configured to provide the audible message.

7. The system as set forth in claim 1, wherein the in-the-ear probe includes:
a tube configured to be inserted into the ear canal of the subject;
a first device disposed on an exterior of the tube and inserted with the tube into the ear canal of the subject, wherein the first device senses at least respiration of the subject; and
a second device disposed on an exterior of the tube and inserted with the tube into the ear canal of the subject, wherein the second device produces an audible message when the respiration cessation is determined, and wherein the audible message stimulates the subject to resume respiration.

8. The system according to claim 1, further including:
a behind-the-ear monitoring device including the analyzing device;
wherein the at least one physiological parameter includes respiration, pulse, and blood oxygen level ($SpO_2$);
wherein the at least one sensor includes a microphone sensing the respiration; and,
wherein the analyzing device is configured to compare a combination of the sensed respiration, the sensed blood oxygen level ($SpO_2$), and the sensed pulse with a combination of physiological thresholds and configured to determine the respiration cessation based on the combined analysis to minimize a number of erroneous stimulations.

9. A method comprising:
inserting an in-the-ear probe which carries sensors and a stimulating device into an auditory canal of a sleeping subject, the in-the-ear probe including an inflatable balloon configured to position at least some of the sensors proximate to tissue within the auditory canal to sense physiological parameters, the at least some of the sensor operatively coupled to a surface of the balloon, the sensors including at least a microphone, light emitting diodes (LEDs) and an infrared (IR) source, and the physiological parameters including at least respiration rate, blood oxygen level ($SpO_2$), and pulse rate;
non-invasively sensing the physiological parameters of the subject within an auditory canal of the subject;
analyzing the sensed respiration rate, the sensed pulse rate, and the sensed blood oxygen level ($SpO_2$) to determine respiration cessation; and,
in response to determining the respiration cessation of the subject, stimulating the subject with the stimulating device in the auditory canal to mitigate the respiration cessation, wherein the stimulating includes providing a subconscious message to the sleeping subject without waking the subject, wherein the subconscious message reminds the subject to breathe and/or to turn onto a subject side.

10. The method as set forth in claim 9, wherein the stimulating includes providing a subconscious message into the auditory canal of the sleeping subject without waking the subject.

11. The method as set forth in claim 9, wherein the step for analyzing includes:
comparing the sensed respiration rate with a physiological threshold.

12. The method as set forth in claim 9, further including:
non-invasively sensing blood pressure with one or more sensors disposed on an exterior of the in-the-ear probe;
wherein the step for analyzing further includes analyzing the sensed blood pressure to determine the respiration cessation.

13. The method as set forth in claim 9, wherein the step for analyzing includes:
comparing the sensed respiration rate, the sensed blood oxygen level ($SpO_2$) and the sensed pulse rate with a combination of physiological thresholds; and
based on a comparison, determining the respiration cessation.

14. The method as set forth in claim 9, wherein the analyzing includes determining obstructive sleep disordered breathing (OSDB) events, and further including:
transmitting at least one of the sensed physiological parameters and determined OSDB events to a computerized unit; and
recording at least one of an entire sleep activity and a number and severity of the OSDB events.

15. The method as set forth in claim 14, further including one of:
performing polysomnographic diagnostic analysis of the recorded OSDB events, and
transferring at least one of the collected and the analyzed data to a Polysomnography Lab for polysomnographic diagnostic analysis.

16. An apparatus for performing the method of claim 9.

17. The method as set forth in claim 9, further including:
inflating the inflatable balloon of the in-the-ear probe after inserting the in-the-ear probe into the auditory canal of the subject, wherein the inflatable balloon positions the sensors proximate to tissue within the auditory canal with adequate pressure to ensure coupling of the sensors with the tissue but without causing decreased perfusion or blanching of the tissue.

18. A system for monitoring and treating obstructive sleep disordered breathing (OSDB) comprising:
an in-the-ear sensing device configured to be disposed within an ear canal of a subject and configured to non-invasively sense a plurality of physiological parameters, including respiration, pulse, and blood oxygen level ($SpO_2$), of the subject with at least one sensor, wherein the physiological parameters are indicative of the OSDB, wherein the at least one sensor includes a microphone sensing the respiration, and wherein the in-the-ear sensing device includes an inflatable balloon configured to position the at least one sensor proximate to tissue within the ear canal upon inflation, the at least one sensor operatively couple to a surface of the balloon;
a behind-the-ear monitoring device operatively coupled to the in-the-ear sensing device to communicate with the in-the-ear sensing device, the behind-the-ear monitoring device including:
an analyzing device configured to analyze the sensed physiological parameter to determine an OSDB event based on the analysis, wherein the analysis includes comparing a combination of the sensed respiration, the sensed pulse, and the sensed blood oxygen level ($SpO_2$) with a combination of physiological thresholds; and
a device disposed in the in-the-ear sensing device configured to stimulate the subject to mitigate the OSDB event, wherein the stimulating is based on the determined OSDB event.

19. The system as set forth in claim 18, wherein the at least one sensor is configured to be positioned on an exterior of the in-the-ear sensing device.

20. The system as set forth in claim 18, wherein the physiological thresholds are selected based on medical history of the subject.

21. The system as set forth in claim 18, wherein the in-the-ear sensing device includes:
a device configured to generate a subconsciously audible signal hearable by the subject, wherein the audible signal urges the subject, without waking the subject, to resume breathing or to turn onto a subject side.

22. The system as set forth in claim 18, further including:
a wireless transceiver, operationally coupled with the monitoring device, configured to wirelessly transmit at least one of the physiological parameter and the determined OSDB event, one of continuously, periodically at a predetermined rate, on-demand, and upon detection of the OSDB event; and
a computerized unit operationally coupled to the transceiver configured to record at least one of an entire sleep activity and a number and severity of the OSDB events.

23. The system as set forth in claim 22, wherein the computerized unit one of performs polysomnographic diagnostic analysis of the recorded OSDB events and electronically transfers one of the recorded and analyzed data to a Polysomnography Lab.

\* \* \* \* \*